(12) United States Patent
Devaux et al.

(10) Patent No.: US 10,364,262 B2
(45) Date of Patent: *Jul. 30, 2019

(54) METHOD FOR THE SYNTHESIS OF N-PHOSPHONOMETHYLIMINODIACETIC ACID

(71) Applicant: MONSANTO TECHNOLOGY LLC, St. Louis, MO (US)

(72) Inventors: Albert Devaux, Mont-saint-guibert (BE); Sebastian Burck, Louvain-la-neuve (BE); Patrick Notte, Wavre (BE)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/415,684

(22) PCT Filed: Jul. 17, 2013

(86) PCT No.: PCT/EP2013/065119
§ 371 (c)(1),
(2) Date: Jan. 19, 2015

(87) PCT Pub. No.: WO2014/012986
PCT Pub. Date: Jan. 23, 2014

(65) Prior Publication Data
US 2015/0166584 A1    Jun. 18, 2015

(30) Foreign Application Priority Data

Jul. 17, 2012  (EP) .................................. 12176749

(51) Int. Cl.
*C07F 9/38*   (2006.01)

(52) U.S. Cl.
CPC .......... *C07F 9/3808* (2013.01); *C07F 9/3813* (2013.01)

(58) Field of Classification Search
CPC .... C07F 9/3808; C07F 9/6533; C07F 9/3873; C07F 9/3886; C07F 9/5726; C07F 9/5728; C07F 9/3813; C07F 9/6524; C08F 8/40
USPC ....... 544/157; 548/412, 415; 562/12, 14, 16, 562/17
See application file for complete search history.

(56) References Cited

U.S. PATENT DOCUMENTS

| | | | |
|---|---|---|---|
| 3,288,846 A | 11/1966 | Irani et al. | |
| 3,451,937 A | 6/1969 | Quimby | |
| 3,455,675 A | 7/1969 | Irani et al. | |
| 3,796,749 A | 3/1974 | Krueger et al. | |
| 3,799,758 A | 3/1974 | Franz et al. | |
| 3,816,517 A * | 6/1974 | Krueger ................. | C07F 9/3817 510/469 |
| 3,832,393 A | 8/1974 | Krueger et al. | |
| 3,927,080 A | 12/1975 | Gaertner | |
| 3,969,398 A | 7/1976 | Hershman | |
| 4,065,491 A | 12/1977 | Pfliegel et al. | |
| 4,211,547 A | 7/1980 | Gaertner | |
| 4,237,065 A * | 12/1980 | Ehrat ..................... | C07F 9/3813 558/135 |
| 4,400,330 A * | 8/1983 | Wong .................... | C07F 9/3813 544/337 |
| 4,407,761 A * | 10/1983 | Blum ...................... | C02F 1/683 252/180 |

(Continued)

FOREIGN PATENT DOCUMENTS

| | | |
|---|---|---|
| CA | 1039739 | 10/1978 |
| CH | 275435 | 5/1951 |

(Continued)

OTHER PUBLICATIONS

Corbridge ("4. Phosphides of Non-Metals" Phosphorus Chemistry, Biochemistry, and Technology, 6th edition, D.E.C Corbridge, Ed, 2013, p. 93-176).*
Bouroujeni ("Synthesis of alpha-aminophosphonates using polystyrene supported Al(OTf)3 as a heterogeneous catalyst" Synthesis and Reactivity in Inorganic Metal-Organic, and Nano-Metal Chemistry, 41, 2011, p. 173-176).*
International Search Report for PCT/EP2013/065119, Completed by the European Patent Office on Sep. 27, 2013, 3 Pages.
Arizpe et al. Eur. J. Org. Chem. 2011, p. 3074-3081, "Stereodivergent synthesis of two a-aminophosphonic acids characterized by a cis-fused octahydroindole system."
Tapia-Benavidis et al. Heterocycles 1997, vol. 45, p. 1679-1686, "Syntheses of N-Substituted 2,5-Piperazindiones."

(Continued)

*Primary Examiner* — Amy C Bonaparte
(74) *Attorney, Agent, or Firm* — Stinson LLP; Erin C. Robert

(57) ABSTRACT

A method for synthesis of N-phosphonoalkyliminodiacetic acid or derivatives thereof by forming a reaction mixture having an acid catalyst, a compound of the following general formula $R^1$—$CH_2$—NX—$CH_2$—$R^2$ and a compound having one or more P—O—P anhydride moieties to form a compound having a formula $R^1$—$CH_2$—N(—$CH_2PO_3R^3{}_2$)(—$CH_2$—$R^2$) wherein in $R^1$—$CH_2$—NX—$CH_2$—$R^2$: X is —$CH_2$—OH or —$CH_2$—COOH; $R^1$ and $R^2$ are independently selected from the group consisting of nitrile, $C_1$-$C_4$ alkyl carboxylate, and carboxylic acid for when X is —$CH_2$—OH, or $R^1$ and $R^2$ are both carbonyl groups linked by a hydrogen substituted nitrogen atom or a $C_1$-$C_4$-alkyl substituted nitrogen atom; and $R^3$ is H, an alkyl group, or an aryl group; the anhydride moieties in the P—O—P anhydride compound have one P atom at the oxidation state (+III) and one P atom at the oxidation state (+III) or (+V); and 2) hydrolyzing the mixture to form N-phosphonomethyliminodiacetic acid or one of its derivatives.

21 Claims, No Drawings

(56) References Cited

U.S. PATENT DOCUMENTS

| | | | |
|---|---|---|---|
| 4,422,982 A | 12/1983 | Subramanian | |
| 4,582,650 A * | 4/1986 | Felthouse | B01J 23/40 502/74 |
| 4,617,415 A | 10/1986 | Balthazor et al. | |
| 4,624,937 A | 11/1986 | Chou | |
| 4,654,429 A | 3/1987 | Balthazor et al. | |
| 4,657,705 A | 4/1987 | Miller et al. | |
| 4,804,499 A | 2/1989 | Miller et al. | |
| 4,931,585 A | 6/1990 | Pelyva et al. | |
| 4,937,376 A * | 6/1990 | Fields, Jr. | C07F 9/3813 562/16 |
| 5,155,257 A * | 10/1992 | Kleiner | C07F 9/3808 562/15 |
| 5,312,972 A * | 5/1994 | Cullen | C07F 9/3808 562/17 |
| 5,312,973 A | 5/1994 | Donadello | |
| 5,688,994 A | 11/1997 | Baysdon et al. | |
| 7,084,298 B2 | 8/2006 | Maase et al. | |
| 9,150,599 B2 | 10/2015 | Burck et al. | |
| 2004/0024180 A1 | 2/2004 | Drauz et al. | |
| 2011/0118502 A1* | 5/2011 | Notte | C07F 9/3817 562/11 |
| 2015/0166584 A1 | 6/2015 | Devaux et al. | |
| 2015/0232493 A1* | 8/2015 | Notte | C07F 9/6533 544/157 |

FOREIGN PATENT DOCUMENTS

| | | |
|---|---|---|
| CH | 620223 | 11/1980 |
| CN | 1631894 | 6/2005 |
| CN | 1285600 | 11/2006 |
| DE | 3903715 | 8/1989 |
| DE | 3903716 | 8/1989 |
| DE | 4026026 | 2/1992 |
| DE | 19909200 | 3/2000 |
| DE | 19914375 | 10/2000 |
| EP | 0480307 | 4/1992 |
| EP | 0537786 | 4/1993 |
| EP | 0595598 | 5/1994 |
| EP | 0638577 | 2/1995 |
| EP | 1681294 | 7/2006 |
| EP | 1681295 | 7/2006 |
| EP | 2112156 | 10/2009 |
| ES | 2018746 | 5/1991 |
| GB | 1142294 | 2/1969 |
| GB | 1230121 | 4/1971 |
| GB | 2154588 | 9/1985 |
| GB | 2154589 | 9/1985 |
| JP | 5775990 | 5/1982 |
| JP | 2007022956 | 2/2007 |
| RO | 101476 | 12/1991 |
| WO | 9415939 | 7/1994 |
| WO | 9422880 | 10/1994 |
| WO | 9640698 | 12/1996 |
| WO | 9819992 | 5/1998 |
| WO | 9835930 | 8/1998 |
| WO | 0002888 | 1/2000 |
| WO | 0009520 | 2/2000 |
| WO | 0014093 | 3/2000 |
| WO | 0192208 | 12/2001 |
| WO | 02055527 | 7/2002 |
| WO | 2006107824 | 10/2006 |
| WO | 2009068636 | 6/2009 |
| WO | 2009130322 | 10/2009 |
| WO | 2010055056 | 5/2010 |
| WO | 2010136574 | 12/2010 |
| WO | WO 2011/039378 * | 4/2011 |
| WO | 2011051309 | 5/2011 |

OTHER PUBLICATIONS

European Search Report for European Application No. 12176749, Completed by the European Patent Office on Jan. 9, 2013, 5 Pages.

Greenwood et al. Chemistry of the Elements, 2nd ed., Chapter 12.3.5, p. 503-510, 1998, "Phosphorus Oxides, Sulfides, Selenides and Related compounds".

Merck Index, entry for nitrilotriacetic acid, downloaded on Jun. 10, 2017, Last revised in 2013, 2 pages, https://www.rce.org/MerckIndex/monograph/m7935/nitrilotriacetic%20aGid?q=authorize.

* cited by examiner

METHOD FOR THE SYNTHESIS OF N-PHOSPHONOMETHYLIMINODIACETIC ACID

CROSS-REFERENCE TO RELATED APPLICATION

This application is the U.S. national phase of PCT Application No. PCT/EP2013/065119 filed on Jul. 17, 2013, which claims priority to EP Patent Application No. 12176749.5 filed on Jul. 17, 2012, the disclosures of which are incorporated in their entirety by reference herein.

FIELD OF THE INVENTION

The present invention is related to the synthesis of N-phosphonomethyliminodiacetic acid or derivatives thereof.

STATE OF THE ART

As disclosed in for example EP0595598 patent N-phosphonomethyliminodiacetic acid in general serves as an intermediate in the preparation of N-(phosphonomethyl) glycine, which is an important broad spectrum herbicide. Furthermore, for N-phosphonomethyliminodiacetic acid itself useful phytotoxicity is reported in for example U.S. Pat. No. 3,455,675.

A typical process for the preparation of N-phosphonomethyliminodiacetic acid is described in example 2, of U.S. Pat. No. 3,455,675 wherein aminodiacetic acid hydrochloride is reacted with formaldehyde and phosphorous acid in the presence of hydrochloric acid; the use of N-phosphonomethyliminodiacetic acid and some of its derivatives as selective phytotoxicant on grasses and other noxious weeds is disclosed.

Many other processes for the manufacture of N-phosphonomethyliminodiacetic acid are known and are already subject to numerous publications.

CH275435 patent discloses a method for the preparation of N-phosphonomethyliminodiacetic acid wherein aminomethylphosphonic acid is reacted with chloroacetic acid at a pH comprised between 9.5 and 11.

DE3903715 patent discloses a process wherein N-phosphonomethyliminodiacetic acid is prepared from the calcium salt of iminodiacetic acid. The calcium salt of iminodiacetic acid is obtained from the addition of calcium hydroxide to a reaction mixture comprising an aqueous solution of chloroacetic acid and ammonia. The iminodiacetic acid calcium salt is then heated with concentrated hydrochloric acid. The iminodiacetic acid hydrogen-chloride, thus obtained, is separated and then dissolved in water and finally reacted with phosphorous acid and with an aqueous solution of formaldehyde.

DE3903716 patent discloses a method for the preparation of N-phosphonomethyliminodiacetic acid and lower alkyl $C_1$-$C_4$ acid chloride, simultaneously prepared by reacting phosphorus trichloride and $C_1$-$C_4$ carboxylic acid. The phosphorous acidic phase containing carboxylic acid and carboxylic acid chloride, after dilution with water, is reacted with iminodiacetic acid and an aqueous solution of formaldehyde in the presence of a strong mineral acid, preferably hydrochloric acid.

ES2018746 patent discloses a process for obtaining N-phosphonomethyliminodiacetic acid which comprises reacting methylene-di-iminodiacetonitrile in an aqueous solution with formaldehyde, phosphorous acid and a strong mineral acid.

U.S. Pat. No. 4,211,547 discloses N-phosphonomethyliminodiaceto nitrile and arylesters and salts thereof, prepared by first forming an alkalimetal salt of aminomethylphosphonic acid and reacting the salt with formaldehyde; thereafter the intermediate product is reacted with potassium cyanide. In a further step, N-phosphonomethyliminodiacetonitrile is converted into N-phosphonomethylimino diacetic acid by acid hydrolysis in hydrochloric acid.

WO02055527 patent application discloses a method for producing N-phosphonomethyliminodiacetic acid by reacting an alkali metal salt of iminodiacetic acid with phosphorus trichloride in an aqueous solution, forming iminodiacetic acid hydrochloride, phosphorous acid and corresponding alkali metal chloride. A reaction then takes place with a formaldehyde source and N-phosphonomethyliminodiacetic acid is obtained from the reaction mixture.

WO0009520 patent application discloses a process wherein N-acetyliminodiacetic acid is either: (1) reacted with a source of phosphorus and a source of formaldehyde in the presence of an acid to form a phosphonomethylation reaction product containing N-phosphonomethyliminodiacetic acid and acetic acid or (2) deacylated and cyclized to form a 2,5-diketopiperazine derivative and then reacted with a source of phosphorus and a source of formaldehyde in the presence of an acid to form a phosphonomethylation reaction product containing N-phosphonomethyliminodiacetic acid and acetic acid. Either way, the N-phosphonomethyliminodiacetic acid is precipitated and the precipitate is recovered.

DE19909200 patent discloses a method for the manufacturing of N-phosphonomethyliminodiacetic acid wherein iminodiacetic acid is reacted with phosphorous acid and formaldehyde in an aqueous medium in the presence of a strong mineral acid.

DE19914375 patent discloses a method for the production of N-phosphonomethyliminodiacetic acid by: (a) neutralizing an aqueous solution of the sodium salt of iminodiacetic acid with a strong mineral acid; (b) separating iminodiacetic acid; (c) reacting iminodiacetic acid with formaldehyde and phosphorous acid in an aqueous solution in the presence of the strong mineral acid and (d) separating N-phosphonomethyliminodiacetic acid thus obtained e.g. by filtration, the mother liquor from (d) is recycled to stage (a).

GB2154588 patent discloses a process for preparation of N-(phosphonomethyl)glycine from N-phosphonomethyliminodiacetic acid, obtained by reacting phosphorous acid, formaldehyde and iminodiacetic acid in stoichiometric ratio and in the presence of hydrochloric acid and using elevated pressure which may be created by heating the reaction mixture under a closed system.

GB2154589 patent discloses a process for preparing N-phosphonomethyliminodiacetic acid which comprises reacting an alkali metal salt of iminodiacetic acid in an aqueous strong mineral acid solution with phosphorous acid and formaldehyde and then adding sufficient water to dissolve the alkali metal salt formed during the reaction.

IE 20020974 patent discloses a process for the manufacture of N-(phosphonomethyl)glycine from N-phosphonomethyliminodiacetic acid, comprising the steps of reacting iminodiacetic acid, phosphorous acid and formaldehyde in the presence of water and hydrochloric acid to give N-phosphonomethyliminodiacetic acid.

U.S. Pat. No. 4,657,705 discloses a process for the preparation of an N-substituted amino methylphosphonic acid comprising reacting a substituted amine, urea or carbamate substrate compound with phosphorous acid and formaldehyde in an acidic medium. In example 2 the synthesis of N-phosphonomethyliminodiacetic acid, obtained from the reaction of an aqueous hydrochloric acid solution of N-acetyliminodiacetic acid, phosphorous acid and formaldehyde, is described.

U.S. Pat. No. 5,312,973 discloses a process for preparing N-phosphonomethyliminodiacetic acid by means of phosphonomethylation of iminodiacetic acid performed by reacting an aqueous solution of phosphorous acid and hydrochloric acid, obtained by hydrolysis of phosphorous trichloride, with iminodiacetic acid and formaldehyde.

WO0002888 patent application discloses a process for the production of N-phosphonomethyliminodiacetic acid wherein an alkali metal salt of iminodiacetic acid is reacted with phosphorous acid and a strong mineral acid, or a source thereof to form iminodiacetic phosphite and the alkali metal salt of the strong mineral acid. After removal of the latter salt, the iminodiacetic phosphite is converted to N-phosphonomethyliminodiacetic acid by reaction with formaldehyde.

WO0014093 patent application discloses a process for the preparation of N-phosphonomethyliminodiacetic acid and N-(phosphonomethyl)glycine wherein an alkali metal of iminodiacetic acid is reacted with a strong mineral acid to convert the salt of iminodiacetic acid into iminodiacetic acid. The iminodiacetic acid is then converted to soluble iminodiacetic acid phosphite salt by the addition of phosphorous acid, and the alkali metal salt of the strong acid is precipitated. The phosphite salt of iminodiacetic acid is phosphonomethylated, such as by the addition of phosphorus trichloride and formaldehyde. N-phosphonomethyliminodiacetic acid, thus obtained, is isolated and can further be oxidized to N-(phosphonomethyl)glycine.

WO9415939 patent application discloses a process for the manufacture of N-phosphonomethyliminodiacetic acid which comprises reacting iminodiacetic acid with phosphorous acid and a source of formaldehyde in aqueous solution in the presence of concentrated sulfuric acid and filtering and recovering the precipitated N-phosphonomethyliminodiacetic acid.

U.S. Pat. No. 5,688,994 discloses a process for the preparation of N-phosphonomethyliminodiacetic acid comprising simultaneously infusing into a reaction mixture, water, a source of iminodiacetic acid, a source of formaldehyde, a source of phosphorous acid and a strong acid. Phosphorous acid and the strong acid preferably are provided to the reaction mixture from a single source preferably phosphorus trichloride.

WO9819992 patent application discloses a method for making solution stable salts of iminodiacetic acid, useful as precursors in the manufacture of N-phosphonomethyliminodiacetic acid. N-phosphonomethyliminodiacetic acid is prepared by adding a strong acid to the di-salt of iminodiacetic acid in order to prepare a stable solution comprising mono-salt of iminodiacetic acid and further reacting said mono-salt of iminodiacetic acid with additional strong acid, phosphorous acid and formaldehyde. The additional strong acid and the phosphorous acid are provided by adding phosphorus trichloride to an aqueous reaction medium.

WO2009130322 patent application discloses a method for the manufacture of aminoalkylenephosphonic acids. Pure tetraphosphorus hexaoxide ($P_4O_6$) is hydrolyzed in the presence of a homogeneous Brønsted acid catalyst whereby the pH of the reaction medium is maintained below 5 and the free water content of said reaction medium is, after the $P_4O_6$ hydrolysis has been completed, from 0 to 40%. The required amine component can be added before, during, or in a preferred embodiment, after the completion of the $P_4O_6$ hydrolysis. Formaldehyde is then added and the reaction mixture containing the tetraphosphorus hexaoxide hydrolysate, the amine and the formaldehyde is reacted in presence of a Brønsted acid catalyst selected from homogeneous and heterogeneous species. In example 2 the synthesis of N-phosphonomethyliminodiacetic acid is described wherein first $P_4O_6$ is drop wise added to a solution of iminodiacetic acid in aqueous hydrochloric acid whereupon an aqueous solution of formaldehyde is drop wise added.

WO2010136574 patent application discloses a method for the manufacture of N-phosphonoalkyliminodiacetic acid wherein the iminodiacetic acid starting material is reacted with a considerable amount, in excess of stoichiometric requirements, of phosphorous acid whereupon formaldehyde is added. In a particularly preferred approach, the phosphorous acid is prepared in situ starting from the hydrolysis of liquid $P_4O_6$, added to an aqueous reaction medium containing phosphorous acid.

WO 2011051309 patent application discloses an improved method for the manufacture of N-phosphonoalkyliminodiacetic acid $M_2PO_3$—X—N—$(CH_2COOM)_2$ wherein X is a $C_1$-$C_6$ linear or branched alkyl group and M is selected from hydrogen, alkali, earth-alkali, ammonium and protonated amine. The iminodiacetic acid starting material is reacted with a substantially stoichiometric amount of phosphorous acid, in the presence of a large excess of phosphoric acid and formaldehyde to thereby yield phosphonoalkyliminodiacetic acid which is insoluble in the reaction medium and thus can be separated from the reaction medium. In a particularly preferred approach, the phosphorous acid is prepared in situ starting from liquid $P_4O_6$, i.e. through the addition of $P_4O_6$ to the aqueous reaction medium, containing preferably a part of the phosphoric acid, in order to be completely hydrolyzed.

EP0595598 patent discloses a process for preparing N-phosphonomethyliminodiacetic acid wherein solutions of an alkali metal salt of iminodiacetic acid are reacted with formaldehyde so as to form the alkali metal salt of hydroxymethyliminodiacetic acid which subsequently is reacted with a phosphorus source such as phosphorous acid. One example illustrates the preparation of N-phosphonomethyliminodiacetic acid starting from an aqueous solution of disodium salt of hydroxymethyl iminodiacetic acid and phosphorus trichloride. The modus operandi implies that all phosphorus trichloride is immediately converted completely in phosphorous acid and hydrogen chloride.

U.S. Pat. No. 4,617,415 claims alpha-substituted N-phosphonomethyl iminodiacetic acids while U.S. Pat. No. 4,654,429 discloses a process for the preparation of a glyphosate product through contacting an aqueous medium of the alpha-substituted N-phosphonomethyliminodiacetic acid substrate with molecular oxygen in the presence of a catalyst for the oxidative cleavage of a substituent from the imino nitrogen of the substrate. Two processes for the preparation of the N-phosphonomethyliminodiacetic acid substrate are described.

In a first method a haloacetic acid is reacted in an alkaline medium with an alpha-substituted amino acid to form an alpha-substituted iminodiacetic acid. Phosphonomethylation is preferably carried out by adding phosphorous acid to an acidic aqueous medium containing the alpha-substituted iminodiacetic acid and a mineral acid, and slowly adding a solution of formaldehyde to the resultant mixture. Essentially stoichiometric equivalent proportions of the alpha-substituted iminodiacetic acid, phosphorous acid, and formaldehyde may be used for the phosphonomethylation.

CN patent 1285600 discloses the preparation of N-phosphonomethyl iminodiacetic acid from the catalytic dehydrogenation of adiethanolamine in the presence of sodium hydroxide and further reacting the iminodiacetic acid, thus formed, with formaldehyde. N-phosphonomethyl iminodiacetic acid subsequently is oxidized with hydrogen peroxide in water, in the presence of sodium tungstate catalyst resulting in the formation of N-(phosphonomethyl) glycine.

In an alternative method aminoacetonitrile is reacted with a cyanohydrin to produce an alpha-substituted iminodiacetonitrile which is subsequently hydrolyzed to produce the alpha-substituted iminodiacetic acid. The latter in turn is converted into the alpha-substituted N-phosphonomethyl-iminodiacetic acid intermediate via the phosphonomethylation reaction as described in the first method of the invention.

The prior art abundantly illustrates the significant difficulties and shortcomings attached to the use of most of the known N-phosphonomethylimino diacetic acid manufacturing technologies. Major difficulties can reside in the selection of the acid catalyst, usually sulfuric and/or hydrochloric acid, the presence of chlorides, frequently alkali chlorides, the formation of undesirable levels of by-products and the lack of selectivity of the reaction product. In addition, N-phosphonomethyliminodiacetic acid produced in accordance with the art technologies, in general requires special precautions in the conversion to N-(phosphonomethyl)glycine, while the corrosive nature of chloride ions can adversely affect equipment economics. While considerable efforts have been spent for the purpose of alleviating quality and economic aspects of the manufacturing technology, marginal solutions, directed to specific shortcomings, have been elaborated.

AIMS OF THE INVENTION

The present invention aims to provide a method for the synthesis of N-phosphonomethyliminodiacetic acid, or derivates thereof, that does not present the drawbacks of the methods of the state of the art, especially a method that is efficient, economical-attractive, environmental-friendly and safe.

SUMMARY OF THE INVENTION

The present invention discloses a method for the synthesis of N-phosphonomethyliminodiacetic acid or derivatives thereof selected from the group consisting of phosphonate esters of N-phosphonomethyliminodiacetic acid, carboxylate esters of N-phosphonomethyliminodiacetic acid, phosphonate and carboxylate esters of N-phosphonomethyliminodiacetic acid, N-phosphonomethyliminodiacetic acid salts, phosphonate esters of N-phosphonomethyliminodiacetic acid salts, carboxylate esters of N-phosphonomethyliminodiacetic acid salts and phosphonate-carboxylate esters of N-phosphonomethyliminodiacetic acid salts, wherein the cation of the salt is selected from the group consisting of ammonium, isopropylammonium, ethanolammonium, dimethylammonium, trimethylsulfonium, sodium and potassium,
comprising the steps of:
a) forming a reaction mixture comprising an acid catalyst, a compound having the general formula $R^1-CH_2-NX-CH_2-R^2$ and a compound having one or more P—O—P anhydride moieties, to form a compound having the general formula $R^1-CH_2-N(-CH_2-PO_3H_2)(-CH_2-R^2)$, its dehydrated forms or their derivatives, wherein the compound of the formula $R^1-CH_2-NX-CH_2-R^2$ is characterized in that:

X is $-CH_2-OH$ or $-CH_2-COOH$;

$R^1$ and $R^2$ are independently selected from the group consisting of nitrile, $C_1$-$C_4$ alkyl carboxylate, or are both carbonyl groups linked by means of a hydrogen substituted nitrogen atom or a $C_1$-$C_4$-alkyl substituted nitrogen atom;

the P—O—P anhydride moieties comprising compound is characterized in that said anhydride moieties comprise one P atom at the oxidation state (+III) and one P atom at the oxidation state (+III) or (+V) and is selected from the group consisting of tetraphosphorus hexaoxide, tetraethylpyrophosphite and the compounds obtained from the combination of one or more compounds comprising;

one or more P—OH moieties with one or more compounds comprising one or more P—O—P anhydride moieties or one or more P—X moieties, wherein the P atom of one or more compounds is at the oxidation state (+III);

one or more P—X moieties and water, wherein the P atom of the P—X moiety comprising compound is at the oxidation stage (+III);

two or more P—O—P moieties and water, wherein the P—O—P moiety comprising compound has a P atom at the oxidation state (+III) and a P atom at the oxidation state (+III) or (+V);

wherein the compounds having one or more P—OH moieties is accessible by tautomerization of a >P(=O)H moiety, wherein X is a halogenide selected from the group consisting of chlorine, bromine and iodine and wherein the halogen level in the P—O—P anhydride moiety comprising compound is 1000 ppm or less, preferably 500 ppm or less and more preferably 200 ppm or less.

b) hydrolyzing the reaction mixture to form N-phosphonomethyliminodiacetic acid or one of its derivatives.

Preferred embodiments of the present invention disclose one or more of the following features:

the $R^1-CH_2-NX-CH_2-R^2$ corresponds to the 4-X-piperazine-2,6-dione or the 4-X-1-($C_1$-$C_4$ alkyl)piperazine-2,6-dione family;

the ratio of N—X moieties to P—O—P anhydride moieties is comprised between 0.3 and 2.0, preferably between 0.5 and 1.5;

the compound having the general formula $R^1-CH_2-NX-CH_2-R^2$ is selected from the group consisting of N-hydroxymethyliminodiacetonitrile, N-hydroxymethylimino-diacetic acid, N-hydroxymethyliminodiacetic acid dimethylester, N-hydroxymethyl-iminodiacetic acid diethylester, N-carboxymethyliminodiacetonitrile, N-carboxymethyliminodiacetic acid dimethylester and N-carboxymethyliminodiacetic acid diethylester;

the compound comprising the P—O—P anhydride moieties is selected from the group consisting of tetraphosphorus hexaoxide, tetraethylpyrophosphite, and the P—O—P anhydride moiety comprising compound obtained from the combination of phosphorous acid and tetraphosphorus hexaoxide, of phosphorous acid and tetraphosphorus decaoxide, of phosphorous acid and phosphorus trichloride, of dimethylphosphite and tetraphosphorus decaoxide, of phosphorus trichloride and water and of tetraphosphorus hexaoxide and water;

the compound comprising the P—O—P anhydride moieties is tetraphosphorus hexaoxide;

the acid catalyst is a homogeneous Brønsted acid catalyst selected from the group consisting of methanesulfonic acid, trifluoromethanesulfonic acid, acetic acid, trifluoroacetic acid, p-toluenesulfonic acid, hydrochloric acid, phosphorous acid, phosphoric acid and mixtures thereof;

the acid catalyst is a heterogeneous Brønsted acid, preferably selected from the group consisting of:
(i) solid acidic metal oxide combinations as such or supported onto a carrier material;
(ii) cation exchange resins selected from the group comprising copolymers of styrene, ethylvinyl benzene and divinyl benzene, functionalized so as to graft SO$_3$H moieties onto the aromatic group and perfluorinated resins carrying carboxylic and/or sulfonic acid groups;
(iii) organic sulfonic, carboxylic and phosphonic Brønsted acids which are substantially immiscible in the reaction medium at the reaction temperature;
(iv) an acid catalyst derived from:
the interaction of a solid support having a lone pair of electrons onto which is deposited an organic Brønsted acid; or
the interaction of a solid support having a lone pair of electrons onto which is deposited a compound having a Lewis acid site; or
heterogeneous solids functionalized by chemical grafting with a Brønsted acid
group or a precursor thereof; and (v) heterogeneous heteropolyacids of the general formula H$_x$PM$_y$O$_z$ wherein P is selected from phosphorus and silicon and M is selected from tungsten and molybdenum and combinations thereof;

the acid catalyst is a homogeneous Lewis acid preferably selected from the group consisting of LiN(CF$_3$SO$_2$)$_2$, Mg(OCF$_3$SO$_2$)$_2$, Al(OCF$_3$SO$_2$)$_3$, Bi(OCF$_3$SO$_2$)$_3$, Sc(OCF$_3$SO$_2$)$_3$;

the acid catalyst is a heterogeneous Lewis acid obtained from the interaction of a homogeneous Lewis acid catalyst and an organic or inorganic polymer compound;

the compound with general formula R$^1$—CH$_2$—NX—CH$_2$—R$^2$ and the compound having one or more P—O—P anhydride moieties are reacted in step a) in the presence of a solvent selected from the group consisting of 1,4-dioxane, toluene, ethyl acetate, acetonitrile, sulfolane, 1-ethyl-3-methyl-imidazolium bis(trifluoromethylsulfonyl) imide, or a mixture thereof;

the P—O—P anhydride moiety comprising compound is gradually added to the compound with general formula R$^1$—CH$_2$—NX—CH$_2$—R$^2$ while maintaining the temperature of step a) below 100° C., preferably at a temperature comprised between 20° C. and 70° C.;

after completion of the addition of the P—O—P anhydride moiety comprising compound, step a) is heated to a temperature comprised between 20° C. and 100° C., preferably between 30° C. and 90° C. and maintained at the said temperature for a period of time comprised between 1 hour and 24 hours;

the hydrolysis of step b), is performed at a temperature comprised between 20° C. and 120° C., preferably between 40° C. and 100° C., for a period comprised between 10 minutes and 24 hours and preferably between 1 hour and 10 hours;

the hydrolysis of step b) is performed under alkali conditions;

DETAILED DESCRIPTION OF THE INVENTION

The present invention provides an efficient, economical and environmental friendly method for the synthesis of N-phosphonomethyliminodiacetic acid or its derivatives.

Under derivatives the present invention understands salts, phosphonate and carboxylate esters of N-phosphonomethyliminodiacetic acid.

The phosphonate and carboxylate esters comprise one or more substituted or unsubstituted hydrocarbyl groups which may be branched or unbranched, saturated or unsaturated and may contain one or more rings. Suitable hydrocarbyls include alkyl, alkenyl, alkynyl and aryl moieties. They also include alkyl, alkenyl, alkynyl and aryl moieties substituted with other aliphatic or cyclic hydrocarbyl groups, such as alkaryl, alkenaryl and alkynaryl.

The substituted hydrocarbyl is defined as a hydrocarbyl wherein at least one hydrogen atom has been substituted with an atom other than hydrogen such as a halogen atom, an oxygen atom to form for example an ether or an ester group, a nitrogen atom to form an amide or a nitrile group or a sulfur atom to form for example a thioether group.

The derivatives of N-phosphonomethyliminodiacetic acid preferably are obtained as such as an outcome of step a) or step b) or can be obtained by further treatment of N-phosphonomethyliminodiacetic acid. Under derivatives the present invention understands salts, phosphonate esters, carboxylate esters, phosphonate ester salts, carboxylate ester salts or phosphonate-carboxylate ester salts of N-phosphonomethyliminodiacetic acid. In the present invention it is understood that the expression N-phosphonomethyliminodiacetic acid comprises all derivatives.

The method of the present invention includes the steps of:
a) reacting, in the presence of an acid catalyst, a compound with general formula R$^1$—CH$_2$—NX—CH$_2$—R$^2$ with a P—O—P anhydride moiety comprising compound to form a compound having the general formula R$^1$—CH$_2$—N(—CH$_2$—PO$_3$H$_2$)(—CH$_2$—R$^2$), its dehydrated forms or their derivatives, wherein
the compound of the formula R$^1$—CH$_2$—NX—CH$_2$—R$^2$ is characterized in that:
X is —CH$_2$—OH or —CH$_2$—COOH and
R$^1$ and R$^2$ are independently selected from the group consisting of nitrile, C$_1$-C$_4$ alkyl carboxylate, or R$^1$ an R$^2$ are both carbonyl groups linked by means of a hydrogen substituted nitrogen atom or a C$_1$-C$_4$-alkyl substituted nitrogen atom, the R$^1$—CH$_2$—NX—CH$_2$—R$^2$ formula thus corresponding to 4-X-piperazine-2,6-dione or 4-X-1-(C$_1$-C$_4$ alkyl)piperazine-2,6-dione, and wherein
the said P—O—P anhydride comprising compound is characterized in that said anhydride moieties comprise one P atom at the oxidation state (+III) and one P-atom at the oxidation state (+III) or (+V); and
b) hydrolyzing the said compound having the general formula R$^1$—CH$_2$—N(—CH$_2$—PO$_3$H$_2$)(—CH$_2$—R$^2$), its dehydrated forms or their derivatives to form N-phosphonomethyliminodiacetic acid or one of its derivatives.

While the P—O—P anhydride moiety comprising compound is preferably selected from the group consisting of tetraphosphorus hexaoxide and partially hydrolyzed species of tetraphosphorus hexaoxide obtained through reaction of 1 mole of tetraphosphorus hexaoxide with 1, 2, 3, 4 or 5 moles of water respectively, it is understood that all compounds comprising at least one P—O—P anhydride group wherein one P-atom is at the oxidation state (+III) and the other P-atom is at the oxidation state (+III) or (+V) can be used for the purpose of the present invention.

Suitable P—O—P anhydride moiety comprising compounds can either comprise a P—O—P anhydride moiety in the compound itself (e.g. $P_4O_6$ or pyrophosphites $(RO)_2P$—O—$P(OR)_2$) or can be generated in situ by combining reagents that will form the required P—O—P anhydride moiety upon combination before reacting with the compound with general formula $R^1$—$CH_2$—NX—$CH_2$—$R^2$.

Suitable reagent combinations are:
a) compounds containing a least one P—OH moiety (also accessible by tautomerization of a >P(=O)H moiety into >P(LP)OH (where LP stands for lone pair of electrons) such as for example is the case for dimethylphosphite $(MeO)_2P(=O)H$) and compounds containing at least one P—O—P anhydride moiety e.g. $P_2O_5$ or $P_4O_6$;
b) compounds containing at least one P—OH moiety and compounds containing at least one P—X (X=Cl, I, Br) moiety;
c) compounds containing at least one P—X moiety and $H_2O$;
d) compounds containing P—O—P anhydride moieties and $H_2O$ for partial hydrolysis.

In case a) and b) it is mandatory that at least in one of the utilized compounds the P-atom is in the oxidation state (+III) whereas in case c) each P-atom has to be in the oxidation state (+III) and in case d) the P—O—P anhydride moieties have one P-atom at the oxidation state (+III) and the other P-atom at the oxidation state (+III) or (+V), in order to form the P—O—P anhydride moiety comprising compound, having one P-atom at the oxidation state (+III) and the other P-atom at the oxidation state (+III) or (+V).

The P—O—P anhydride moiety comprising compounds wherein the P—O—P anhydride moiety is already present are phosphorus oxides with the formula $P_4O_n$ with n=6-9, pyrophosphites with the general formula $(RO)_2P$—O—$P(OR)_2$ wherein R is an alkyl or aryl group, pyrophosphorous acid $(H_4P_2O_5)$ and isohypophosphoric acid $(H)(HO)P(O)$—O—$P(O)(OH)_2$.

Combinations described under a) are obtained by reacting e.g. phosphorus oxides with formula $P_4O_n$ with n=6-10, alkyl substituted pyrophosphites, pyrophosphorous acid, isohypophosphoric acid, metaphosphoric acid or polyphosphoric acid with phosphorous acid, phosphoric acid, mono or disubstituted phosphites with formula $(RO)PO_2H_2$ or $(RO)_2POH$ wherein R is an alkyl or aryl group, phosphate esters $(RO)PO_3H_2$ or $(RO)_2PO_2H$, phosphonic acids $RPO_3H_2$ or its monoester $RPO_2H(OR)$ with the proviso that such combinations will lead to P—O—P anhydride moiety comprising compounds having one P-atom at the oxidation state (+III) and the other P-atom at the oxidation state (+III) or (+V).

Combinations described under b) are obtained by combining $PCl_3$, $PBr_3$, $POCl_3$, mono or dichloro phosphites like $(RO)_2PCl$ and $(RO)PCl_2$ with phosphorous acid, phosphoric acid, mono or disubstituted phosphites with formula $(RO)PO_2H_2$ or $(RO)_2POH$ with the proviso that such combinations will lead to P—O—P anhydride moiety comprising compounds having one P-atom at the oxidation state (+III) and the other P-atom at the oxidation state (+III) or (+V).

Combinations described under c) are obtained by combining $PCl_3$, $PBr_3$, mono or dichloro phosphites like $(RO)_2PCl$ and $(RO)PCl_2$ with $H_2O$. In order to obtain a P—O—P anhydride moiety comprising compound free of P—X functions the remaining P—X functions are hydrolyzed with water. Remaining P—O—P anhydride moieties can also be hydrolyzed as long as the required P—O—P anhydride moiety wherein one P-atom is at the oxidation state (+III) and the other P-atom is at the oxidation state (+III) or (+V) remains.

Most preferred species are tetraphosphorus hexaoxide, tetraethylpyrophosphite, and the combinations of phosphorous acid and tetraphosphorus hexaoxide, of phosphorous acid and tetraphosphorus decaoxide, of phosphorous acid and phosphorus trichloride, of dimethylphosphite and tetraphosphorus decaoxide, of phosphorus trichloride and water and of tetraphosphorus hexaoxide and water.

The amount of 'reactive' P(+III) atoms that can be converted into phosphonic acids according to this invention is determined by the amount of P(+III) atoms and the amount of P—O—P anhydride moieties. If there are more P—O—P anhydride moieties than P(+III) atoms, then all P(+III) atoms are converted into phosphonic acids. If there are less P—O—P anhydride moieties than P(+III) atoms, then only a part of P(+III) atoms equal to the amount of P—O—P anhydride moieties is converted into phosphonic acids.

If halogen containing starting materials, e.g. $PCl_3$, $POCl_3$ or $PBr_3$, are used, the level of halogen in the P—O—P anhydride comprising compound shall be kept below 1000 ppm, usually below 500 ppm, preferably below 200 ppm, expressed in relation to the P—O—P material being 100%. Therefore all excess P—X functions are hydrolyzed before the reactions with the substrate by addition of one molecule of $H_2O$ per excess of P—X function. The formed H—X is removed by e.g. blowing a dry inert gas, like nitrogen or helium, through the solution.

The tetraphosphorus hexaoxide preferably used within the scope of the present invention may be represented by a substantially pure compound containing at least 85%, preferably more than 90%, more preferably at least 95% and in one particular execution at least 97% of $P_4O_6$. While tetraphosphorus hexaoxide, suitable for use within the context of this invention, may be manufactured by any known technology, in preferred executions it is prepared in accordance with the method described in WO 2009/068636 and/or WO 2010/055056 patent applications under the section entitled "Process for the manufacture of $P_4O_6$ with improved yield." In detail, oxygen, or a mixture of oxygen and inert gas, and gaseous or liquid phosphorus are reacted in essentially stoichiometric amounts in a reaction unit at a temperature in the range from about 1600 K to about 2000 K, by removing the heat created by the exothermic reaction of phosphorus and oxygen, while maintaining a preferred residence time of from about 0.5 seconds to about 60 seconds followed by quenching the reaction product at a temperature below 700 K and refining the crude reaction product by distillation. The tetraphosphorus hexaoxide so prepared is a pure product containing usually at least 97% of the oxide. The so produced $P_4O_6$ is generally represented by a liquid material of high purity containing in particular low levels of elementary phosphorus, $P_4$, preferably below 1000 ppm, expressed in relation to the $P_4O_6$ being 100%. The preferred residence time is from 5 seconds to 30 seconds, more preferably from 8 seconds to 30 seconds. The reaction product can, in one preferred execution, be quenched to a temperature below 350 K.

It is presumed that the $P_4O_6$ participating in a reaction at a temperature of from about 24° C. (melting t°) to about 120° C. is necessarily liquid or gaseous although solid species can, academically speaking, be used in the preparation of the reaction medium.

For reasons of convenience and operational expertise, the tetraphosphorus hexaoxide, represented by $P_4O_6$, is of high purity and contains very low levels of impurities, in particular elemental phosphorus, $P_4$, at a level below 1000 ppm, usually below 500 ppm and preferably not more than 200 ppm, expressed in relation to the $P_4O_6$ being 100%.

In the present invention it is understood that when using the terminology "P—O—P anhydride moiety comprising compound" it is meant "P—O—P anhydride moiety comprising compound wherein one P atom is at the oxidation state (+III) and the other P atom is at the oxidation state (+III) or (+V).

The compound with general formula $R^1$—$CH_2$—NX—$CH_2$—$R^2$ is characterized in that:

X is —$CH_2$—OH or —$CH_2$—COOH $R^1$ and $R^2$ are independently selected from the group consisting of nitrile, $C_1$-$C_4$ alkyl carboxylate, or are both carbonyl groups linked by means of a hydrogen substituted nitrogen or a $C_1$-$C_4$-alkyl substituted nitrogen atom, the $R^1$—$CH_2$—NX—$CH_2$—$R^2$ formula thus corresponding to 4-X-piperazine-2,6-dione or 4-X-1-($C_1$-$C_4$ alkyl)piperazine-2,6-dione.

The compound with general formula $R^1$—$CH_2$—NX—$CH_2$—$R^2$ is preferably selected from the group consisting of N-hydroxymethyliminodiacetonitrile, N-hydroxymethyliminodiacetic acid, N-hydroxymethyliminodiacetic acid dimethyl ester, N-hydroxymethyliminodiacetic acid diethylester, N-hydroxymethyliminodiacetic acid dipropylester, N-hydroxymethyliminodiacetic acid diisopropylester, N-hydroxymethyliminodiacetic acid di-butylester, N-hydroxymethyliminodiacetic acid di-isobutylester, N-hydroxymethyliminodiacetic acid di-sec-butylester, N-hydroxymethyliminodiacetic acid di-tert-butylester, 4-hydroxymethylpiperazine-2,6-dione, 4-hydroxymethyl-1-methylpiperazine-2,6-dione, 4-hydroxymethyl-1-ethylpiperazine-2,6-dione, 4-hydroxymethyl-1-propylpiperazine-2,6-dione, 4-hydroxymethyl-1-isopropylpiperazine-2,6-dione, 4-hydroxymethyl-1-butylpiperazine-2,6-dione, 4-hydroxymethyl-1-isobutylpiperazine-2,6-dione, 4-hydroxymethyl-1-sec-butylpiperazine-2,6-dione, 4-hydroxymethyl-1-tert-butylpiperazine-2,6-dione, N-carboxymethyliminodiacetonitrile, N-carboxymethyliminodiacetic acid dimethylester, N-carboxymethyliminodiacetic acid diethylester, N-carboxymethyliminodiacetic acid dipropylester, N-carboxymethyliminodiacetic acid diisopropylester, N-carboxymethyliminodiacetic acid di-butylester, N-carboxymethyliminodiacetic acid di-isobutylester, N-carboxymethyliminodiacetic acid di-sec-butylester, N-carboxymethyliminodiacetic acid di-tert-butylester, 4-carboxymethylpiperazine-2,6-dione, 4-carboxymethyl-1-methylpiperazine-2,6-dione, 4-carboxymethyl-1-ethylpiperazine-2,6-dione, 4-carboxymethyl-1-propylpiperazine-2,6-dione, 4-carboxymethyl-1-isopropylpiperazine-2,6-dione, 4-carboxymethyl-1-butylpiperazine-2,6-dione, 4-carboxymethyl-1-isobutylpiperazine-2,6-dione, 4-carboxymethyl-1-sec-butylpiperazine-2,6-dione and 4-carboxymethyl-1-tert-butylpiperazine-2,6-dione.

The compound having the general formula $R^1$—$CH_2$—NX—$CH_2$—$R^2$ wherein X is —$CH_2$—OH may be prepared by reacting $R^1$—$CH_2$—NH—$CH_2$—$R^2$ and formaldehyde in the presence of an acid catalyst and optionally a solvent.

The compound having the general formula $R^1$—$CH_2$—NX—$CH_2$—$R^2$ wherein X is —$CH_2$—COOH may be prepared by reacting $R^1$—$CH_2$—NH—$CH_2$—$R^2$ and chloroacetic acid in an alkaline medium.

The acid catalyst preferably used within the scope of the present invention is a homogeneous Brønsted acid catalyst, optionally in the presence of a solvent, or a heterogeneous Brønsted acid catalyst, in the presence of a solvent, or a Lewis acid catalyst, in the presence of a solvent.

The homogeneous Brønsted acid is preferably selected from the group consisting of methanesulfonic acid, fluoromethanesulfonic acid, trichloromethanesulfonic acid, trifluoromethanesulfonic acid, acetic acid, trifluoroacetic acid, tert-butyl-sulfonic acid, p-toluenesulfonic acid, naphthalene sulfonic acid, 2,4,6-trimethylbenzene-sulfonic acid, perfluoro or perchloro alkyl sulfonic acids, perfluoro or perchloro alkyl carboxylic acids, hydrochloric acid, hydrobromic acid, hydroiodic acid, phosphorous acid and phosphoric acid, and mixtures thereof. The homogeneous Brønsted acid is preferably methanesulfonic acid.

The heterogeneous Brønsted acid is preferably selected from the group consisting of:

(i) solid acidic metal oxide combinations as such or supported onto a carrier material;

(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;

(iii) organic sulfonic, carboxylic and phosphonic Brønsted acids which are substantially immiscible in the reaction medium at the reaction temperature;

(iv) an acid catalyst derived from:
  the interaction of a solid support having a lone pair of electrons onto which is deposited an organic Brønsted acid; or
  the interaction of a solid support having a lone pair of electrons onto which is deposited a compound having a Lewis acid site; or
  heterogeneous solids functionalized by chemical grafting with a Brønsted acid group or a precursor therefore; and (v) heterogeneous heteropolyacids of the general formula $H_xPM_yO_z$ wherein P is selected from phosphorus and silicon and M is selected from tungsten and molybdenum and combinations thereof.

Preferred homogeneous Lewis acids can be selected from metal salts having the general formula $MX_n$, wherein M represents a main group element or transition metal like Li, B, Mg, Al, Bi, Fe, Zn, La, Sc, Yb, or Pd; X in $MX_n$ is typically an anion of an acid or acid derivative like Cl, OTf or $NTf_2$, where Tf stands for $CF_3SO_2^-$ and n is equal to the oxidation state of M, which can be from 1 to 5. Possible combinations are e.g. $LiNTf_2$, $Mg(OTf)_2$, $MgCl_2$, $ZnCl_2$, $PdCl_2$, $Fe(OTf)_3$, $Al(OTf)_3$, $AlCl_3$, $Bi(OTf)_3$, $BiCl_3$, $Sc(OTf)_3$, $Ln(OTf)_3$, $Yb(OTf)_3$. Preferably, combinations of a hard metal or a metal on the borderline between hard and soft according to the HSAB (hard soft acid base) concept like Li, Mg, Al, Sc, Zn, Bi, and weekly coordinating anions like OTf or $NTf_2$ are used. Examples of such preferred combinations are: $LiNTf_2$, $Mg(OTf)_2$, $Al(OTf)_3$, $Bi(OTf)_3$.

Preferred heterogeneous Lewis acids can be represented by species of discretionary selected subclasses created by interaction/bonding of homogeneous Lewis acids e.g. metal complexes, metal salts or organometallic species with polymeric organic or inorganic backbones. An example of such subclass is a polystyrene matrix with bonded $Sc(OTf)_2$ groups. Such catalyst can be prepared e.g. by interaction of a polystyrene sulfonic acid resin, e.g. Amberlyst 15, with $Sc(OTf)_3$. The number of equivalents of Lewis acid functions can be determined in this case by different ways e.g. by acid base determination of the unreacted sulfonic acid groups, by quantitative determination of the liberated triflic acid and by ICP measurement of the amount of Sc on the resin.

Typical examples of suitable solvents, optionally used in the method according to the present invention, are anisole; chlorinated and fluorinated hydrocarbons such as fluorobenzene, chlorobenzene, tetrachloroethane, tetrachloroethylene, dichloroethane, dichloromethane; polar solvents like diglyme, glyme, diphenyloxide, polyalkylene glycol derivatives with capped OH groups such as OR* where R* is a low alkyl or acyl group, aliphatic hydrocarbons such as hexane, heptane, cyclohexane; non-cyclic ethers like dibutyl ether, diethyl ether, diisopropyl ether, dipentylether, and butylmethylether cyclic ethers like tetrahydrofuran, dioxane, and tetrahydropyran; mixed cyclic/non-cyclic ethers like cyclopentylmethylether; cyclic and non-cyclic sulfones like sulfolane, aromatic solvents like toluene, benzene, xylene; organic acetates like ethylacetate; organic nitriles like acetonitrile, benzonitrile; silicon fluids like polymethylphenyl siloxane or mixtures thereof; non-reactive ionic liquids like 1-n-butyl-imidazolium trifluoromethanesulfonate, and 1-ethyl-3-methyl-imidazolium bis(trifluoromethyl sulfonyl) imide or a mixture thereof.

In a particular embodiment of the present invention the acid catalyst acts as catalyst and as solvent.

In step a) of the process of the present invention, the P—O—P anhydride moiety comprising compound and the compound with general formula $R^1$—$CH_2$—NX—$CH_2$—$R^2$ are gradually mixed at a temperature of about 100° C. or less.

With the terminology "gradually mixed" the present invention understands:
 the gradual addition of the P—O—P anhydride moiety comprising compound to the compound with general formula $R^1$—$CH_2$—NX—$CH_2$—$R^2$,
 the gradual addition of the compound with general formula $R^1$—$CH_2$—NX—$CH_2$—$R^2$ to the P—O—P anhydride moiety comprising compound,
 the simultaneous gradual addition of the P—O—P anhydride moiety comprising compound and the compound with general formula $R^1$—$CH_2$—NX—$CH_2$—$R^2$ each at independent rate into a medium where reaction between both compounds may proceed.

In general, the P—O—P anhydride moiety comprising compound, preferable tetraphosphorus hexaoxide, is gradually added to the compound with general formula $R^1$—$CH_2$—NX—$CH_2$—$R^2$ while the temperature is maintained at a value of about 100° C. or less and preferably at a temperature comprised between about 20° C. and about 70° C. Once the addition completed, step a) is maintained at a temperature comprised between about 20° C. and about 100° C., preferably between about 30° C. and about 90° C. for a period of time comprised between about 1 hour and about 24 hours.

During the conversion of the compound with general formula $R^1$—$CH_2$—NX—$CH_2$—$R^2$, wherein X is —$CH_2$—COOH, one equivalent of carbon monoxide will be formed for each converted —$CH_2$—COOH equivalent. Carbon monoxide will leave the reaction mixture as a gas of very high purity. This carbon monoxide gas can be used in many applications like e.g. as a fuel, in combination with hydrogen for methanol and Fischer-Tropsch hydrocarbons manufacture, for hydroformylation reactions, for alcohol carbonylation e.g. carbonylation of methanol to acetic acid or the conversion of methyl acetate to acetic anhydride.

After completion of the conversion of $R^1$—$CH_2$—NX—$CH_2$—$R^2$ into $R^1$—$CH_2$—N(—$CH_2$—$PO_3H_2$)(—$CH_2$—$R^2$) in step a), water is optionally added in step b) in order to hydrolyze unreacted P—O—P anhydride moieties, if present, and to convert, N-phosphonomethyliminodiacetonitrile, N-phosphonomethyliminodiacetic acid di-($C_1$-$C_4$)alkylester, 4-phosphonomethyl-piperazine-2,6-dione or 4-phosphonomethyl-1-($C_1$-$C_4$ alkyl)piperazine-2,6-dione into N-phosphonomethyliminodicarboxylic acid.

Unreacted P—O—P anhydride moieties may be the result of an incomplete conversion or of an out of stoichiometric amount of P—O—P anhydride group comprising compounds, i.e. an excess of P—O—P anhydride moieties relative to the N—X equivalents.

Preferably, water is added after completion of step a) and after step a) is cooled down to room temperature. Alternatively step a), after being completed, can be cooled down through the addition of the water. This hydrolysis is performed at a temperature comprised between about 20° C. and about 100° C., preferably between about 40° C. and about 100° C., for a period comprised between about 10 minutes and about 24 hours and preferably between about 1 hour and about 10 hours.

When the hydrolysis is performed under alkali conditions the alkali aqueous solution used is preferably obtained from a base selected from the group consisting of alkali hydroxides, alkaline earth hydroxides, ammonia and primary aliphatic amines; preferably said base is sodium hydroxide or potassium hydroxide.

When the hydrolysis is performed under acid conditions the acid aqueous solution used is preferably obtained from a mineral acid; preferably said mineral acid is volatile and most preferable this acid is hydrochloric acid.

The N-phosphonomethyliminodiacetic acid may be recovered from step b) through precipitation. Precipitation can be facilitated by the cooling of step b). Numerous well known methods, such as for example filtration, can be used to recover the precipitate.

The method of the present invention can be utilized in any reactor system known in the art including batch reactors, continuous reactors or semi-continuous reactors.

EXAMPLES

The following examples illustrate the invention; they are merely meant to exemplify the present invention, but are not destined to limit or otherwise define the scope of the present invention.

Example 1

In a round-bottom flask equipped with a mechanical stirrer, a thermometer and a condenser 1.53 g (10.0 mmole) N,N-biscyanomethyl glycine and 2.0 g (10.0 mmole of $H^+$) Amberlyst 15 were mixed with 5 ml acetonitrile and heated to 60° C. Slowly, 0.55 g (2.5 mmole) $P_4O_6$ was added. The reaction mixture was heated for 3 hours at 60° C. During the addition and reaction time the evolution of CO was observed. 2 ml $H_2O$ was added and afterwards the pH was brought to above 10 by addition of a NaOH solution. The obtained solution was heated for 24 hours at 60° C. The obtained solution was analysed by $^1$H- and $^{31}$P-NMR spectroscopy. N-Phosphonomethyliminodiacetic acid was detected at 80.5% by weight. The ratio of mmoles N,N-biscyanomethyl glycine to mmoles $P_4O_6$ equals 4.0; the ratio of milliequivalents Amberlyst 15 to mmoles N,N-biscyanomethyl glycine equals 1.0; the ratio of milliequivalents Amberlyst 15 to mmoles $P_4O_6$ equals 4.0.

In table 1 a series of examples (Example 2 to 12), according to the present invention, is reported.

In this table:

Column 1: indicates the identification number of the example.
Column 2: indicates the type of compound with general formula $R^1$—$CH_2$—NX—$CH_2$—$R^2$
Column 3: indicates the number of mmoles of compound with general formula $R^1$—$CH_2$—NX—$CH_2$—$R^2$
Column 4: indicates the type of catalyst and solvent if present.
Column 5: indicates the number of mmoles of catalyst.
Column 6: indicates the number of mmoles of tetraphosphorus hexaoxide.
Column 7: indicates the ratio of mmoles of $R^1$—$CH_2$—NX—$CH_2$—$R^2$ compound to mmoles of tetraphosphorus hexaoxide
Column 8: indicates the ratio of mmoles of catalyst to mmoles of $R^1$—$CH_2$—NX—$CH_2$—$R^2$ compound.
Column 9: indicates the ratio of mmoles catalyst to mmoles of tetraphosphorus hexaoxide.
Column 10: indicates the temperature (° C.) for the gradually mixing the constituents of step a).
Column 11: indicates the temperature (° C.) and time (hrs) conditions for completion of step a).
Column 12: indicates the temperature (° C.) and time (hrs) conditions for completion of step b).
Column 13: indicates the reaction yield, in % by weight, as measured by $^1$H-NMR and $^{31}$P-NMR spectroscopy.

Example 13

In a round-bottom flask equipped with a mechanical stirrer, a thermometer and a condenser 10.64 g (80.0 mmole) iminodiacetic acid and 2.40 g (26.7 mmole) 1,3,5-trioxane were mixed with 50 ml acetic acid and heated to 100° C. for 6 hours to form a reaction mixture comprising N-hydroxymethyliminodiacetic acid. After cooling to ambient temperature 4.40 g (20.0 mmole) $P_4O_6$ was added slowly. Then the reaction mixture was heated for 5 hours at to 50° C. The obtained solution was analysed by $^1$H- and $^{31}$P-NMR spectroscopy. N-Phosphonomethyliminodiacetic acid was detected at 19.8% by weight.

Example 14

In a round-bottom flask equipped with a mechanical stirrer, a thermometer and a condenser 7.76 g (80.0 mmole) iminodiacetonitrile and 2.40 g (26.7 mmole) 1,3,5-trioxane were mixed with 50 ml acetic acid and heated to 80° C. for 5 hours. After cooling to ambient temperature 4.40 g (20.0 mmole) $P_4O_6$ was added slowly. Then the reaction mixture was heated for 6 hours at to 80° C. 10 ml $H_2O$ was added and the mixture was heated for 6 hours to 100° C. The obtained solution was analysed by $^1$H- and $^{31}$P-NMR spectroscopy. N-Phosphonomethylimino diacetic acid was detected at 18.6% by weight.

Example 15

In a round-bottom flask equipped with a mechanical stirrer, a thermometer and a condenser 15.14 g (80.0 mmole) diethyl iminodiacetic acid and 2.40 g (26.7 mmole) 1,3,5-trioxane were mixed with 50 ml acetic acid and heated to 80° C. for 6 hours. After cooling to ambient temperature 4.40 g (20.0 mmol) $P_4O_6$ was added slowly. Then the reaction mixture was heated for 8 hours at to 80° C. 10 ml $H_2O$ was added and the mixture was heated for 6 hours to 100° C. The obtained solution was analysed by $^1$H- and $^{31}$P-NMR spectroscopy. N-Phosphonomethylimino diacetic acid was detected at 53.0% by weight.

Example 16

In a round-bottom flask equipped with a mechanical stirrer, a thermometer and a condenser, 1.30 g (8 mmole) N-hydroxymethyliminodiacetic acid, obtained as in example 13, was mixed with 5 ml (78 mmole) methanesulfonic acid. Slowly, 4.20 g (16 mmole) tetraethylpyrophosphite was added. Afterwards the reaction mixture was heated to 60° C. for 8 hours. Then 5 ml water was added and the mixture was stirred at 85° C. for 1 hour. The yield of N-phosphonomethyliminodiacetic acid was 52.1%, as determined by $^1$H- and $^{31}$P-NMR spectroscopy.

Example 17

In a round-bottom flask equipped with a mechanical stirrer, a thermometer and a condenser, 6 ml of methanesulfonic acid, 0.97 g (8.8 mmole) of dimethylphosphite and 0.85 g (6 mmole) of $P_2O_5$ were mixed for 20 minutes at 85° C. Then 1.63 g (10 mmole) N-hydroxymethyliminodiacetic acid, obtained as in example 13, was added and the reaction mixture was heated to 85° C. overnight. Then 5 ml of water was added and the mixture was stirred at 85° C. for 1 hour. The yield of N-phosphonomethyliminodiacetic acid was 42.5%, as determined by $^1$H- and $^{31}$P-NMR spectroscopy.

Example 18

In a round-bottom flask equipped with a mechanical stirrer, a thermometer and a condenser, 6 ml (92.4 mmole) of methanesulfonic acid, 1.8 g (22 mmole) of phosphorous acid and 0.3 ml (2.6 mmole) of $P_4O_6$ were premixed for 20 min at 85° C. Then 1.63 g (10 mmole) N-hydroxymethyliminodiacetic acid, obtained as in example 13, was added and the reaction mixture was heated to 85° C. overnight. Then 5 ml of water was added and the mixture was stirred at 85° C. for 1 hour. The yield of N-phosphonomethyliminodiacetic acid was 15.7%, as determined by $^1$H- and $^{31}$P-NMR spectroscopy.

Example 19

In a round-bottom flask equipped with a mechanical stirrer, a thermometer and a condenser, 10 ml (154 mmole) methanesulfonic acid, 1.64 g (20 mmole) of phosphorous acid and 2.80 g (20 mmole) of $P_2O_5$ were mixed for 1 hour above 50° C. Then 1.63 g (10 mmole) N-hydroxymethyliminodiacetic acid, obtained as in example 13, was added and the reaction mixture was heated to 85° C. overnight. Then 6 ml of water was added and the mixture was stirred at 85° C. for 1 hour. The yield of N-phosphonomethyliminodiacetic acid was 44.0%, as determined by $^1$H- and $^{31}$P-NMR spectroscopy.

Example 20

In a round-bottom flask equipped with a mechanical stirrer, a thermometer and a condenser, 10 ml (154 mmole) methanesulfonic acid, 1.8 ml (22 mmole) of dimethylphosphite and 2.8 g (20 mmole) of $P_2O_5$ were mixed for 1 hour above 50° C. Then 1.63 g (10 mmole) N-hydroxymethyl-iminodiacetic acid, obtained as in example 13, was added and the reaction mixture was heated to 85° C. overnight. Then 6 ml of water was added and the mixture was stirred at 85° C. for 1 hour. The yield of N-phosphonomethyliminodiacetic acid was 61.0%, as determined by $^1$H- and $^{31}$P-NMR spectroscopy.

Example 21

In a round-bottom flask equipped with a mechanical stirrer, a thermometer and a condenser, 0.82 g (10 mmole) phosphorous acid was mixed with 5 ml (78 mmole) methanesulfonic acid. Slowly 1.37 g (10 mmole) PCl$_3$ was added, followed by 1.63 g (10 mmole) N-hydroxymethyliminodiacetic acid, obtained as in example 13. Afterwards the reaction mixture was stirred for 6 hours at 60° C. At ambient temperature 0.5 ml water was added and the mixture was kept standing for 1 hour. The yield of N-phosphonomethyliminodiacetic acid was 39.7%, as determined by $^1$H- and $^{31}$P-NMR spectroscopy.

formula $R^1$—CH$_2$—NX—CH$_2$—$R^2$ and a compound having one or more P—O—P anhydride moieties, to form a compound having the general formula $R^1$—CH$_2$—N(—CH$_2$PO$_3$R$^3_2$)(—CH$_2$—$R^2$), wherein in the compound of the formula $R^1$—CH$_2$—NX—CH$_2$—$R^2$:

X is —CH$_2$—COOH and $R^1$ and $R^2$ are each independently nitrile or C$_1$-C$_4$ alkyl carboxylate, or $R^1$ and $R^2$ are both carbonyl groups linked by means of a hydrogen substituted nitrogen atom or a C$_1$-C$_4$-alkyl substituted nitrogen atom; or X is —CH$_2$—OH and R$_1$ and R$_2$ are each independently nitrile, C$_1$-C$_4$ carboxylate, or carboxylic acid, or $R^1$ and $R^2$ are both carbonyl groups linked by means of a hydrogen substituted nitrogen atom or a C$_1$-C$_4$-alkyl substituted nitrogen atom;

and wherein in the compound having the general formula $R^1$—CH$_2$—N(—CH$_2$PO$_3$R$^3_2$)(—CH$_2$—$R^2$), $R^3$ is H, an alkyl group; and the P—O—P anhydride moieties comprising compound is a compound wherein at least one of the one or more

TABLE 1

| Ex | R$_1$—CH$_2$—NX—CH$_2$—R$^2$ | (mmole) | Catalyst/Solvent | Cata (mmole) | P$_4$O$_6$ (mmole) | X/P$_4$O$_6$ | Cata/X | Cata/P$_4$O$_6$ | T$_1$/° C. | T$_2$/time ° C./hrs | T$_3$/time ° C./hrs | Yield |
|---|---|---|---|---|---|---|---|---|---|---|---|---|
| 2 | N,N-biscyanomethyl glycine | 65.4 | Methanesulfonic acid | 246 | 16.3 | 4.0 | 3.8 | 15.0 | 40 | 70/5 | 25 | 39.3 |
| 3 | N,N-biscyanomethyl glycine | 65.4 | Methanesulfonic acid Acetonitrile (50 ml) | 131 | 16.3 | 4.0 | 2.0 | 8.0 | 25 | 30/2 | 25 | 15.1 (1*) |
| 4 | N,N-biscyanomethyl glycine | 65.4 | Trifluoromethanesulfonic acid Acetonitrile (50 ml) | 130 | 16.3 | 4.0 | 2.0 | 8.0 | 25 | 30/4 | 100/7 | 86.1 |
| 5 | N,N-biscyanomethyl glycine | 65.4 | Methanesulfonic acid Acetonitrile (50 ml) | 196 | 16.3 | 4.0 | 3.0 | 12.0 | 25 | 40/5 25/16 | 90/7 | 97.3 |
| 6 | N,N-biscyanomethyl glycine | 20.0 | Trifluoromethanesulfonic acid Acetonitrile (10 ml) | 10 | 5.0 | 4.0 | 0.5 | 2.0 | 30 | 30/3 | — | 13.4 (2*) |
| 7 | N,N-biscyanomethyl glycine | 10.0 | Methanesulfonic acid | 77 | 2.5 | 4.0 | 7.7 | 31.0 | 25 | 25/3 | 60/24 | 74.0 (3*) |
| 8 | N,N-biscyanomethyl glycine | 10.0 | Trifluoroacetic acid | 65 | 2.5 | 4.0 | 6.5 | 26.0 | 50 | 50/3 | 60/24 | 74.8 (4*) |
| 9 | N,N-biscyanomethyl glycine | 10.0 | Aluminium triflate Acetonitrile (5 ml) | 0.25 | 2.5 | 4.0 | 0.03 | 0.1 | 60 | 60/3 | 60/24 | 75.7 (5*) |
| 10 | N-hydroxymethyl Iminodiacetic acid | 80.0 | Acetic acid | 873 | 20.0 | 4.0 | 10.9 | 43.7 | 25 | 50/5 | — | 19.8 |
| 11 | N-hydroxymethyl Iminodiacetic acid | 80.0 | Acetic acid | 873 | 20.0 | 4.0 | 10.9 | 43.7 | 25 | 80/6 | 100/6 | 18.6 |
| 12 | N-hydroxymethylimino diacetic acid diethylester | 80.0 | Acetic acid | 873 | 20.0 | 4.0 | 10.9 | 43.7 | 25 | 80/8 | 100/6 | 53.0 |

(1*): the oil obtained after completion of the hydrolysis comprises 37.6% weight of N,N-biscyanomethylaminomethylphosphonic acid and 15.1% weight of N-phosphonomethyliminodiacetic.
(2*): in the synthesis of Example 6, no hydrolysis step is performed; finally 65.3% weight of N-phosphonomethyliminodiacetonitrile and 13.4% weight of N-phosphonomethyliminodiacetic acid is formed.
(3*) to (5*): for the hydrolysis, the pH is brought to a value above 10 through the addition of sodium hydroxide.

The invention claimed is:

1. A method for synthesis of N-phosphonomethyliminodiacetic acid or derivatives thereof selected from the group consisting of phosphonate esters of N-phosphonomethyliminodiacetic acid, carboxylate esters of N-phosphonomethyliminodiacetic acid, phosphonate and carboxylate esters of N-phosphonomethyliminodiacetic acid, N-phosphonomethyliminodiacetic acid salts, phosphonate esters of N-phosphonomethyliminodiacetic acid salts, carboxylate esters of N-phosphonomethyliminodiacetic acid salts and phosphonate-carboxylate esters of N-phosphonomethyliminodiacetic acid salts, wherein a cation of the salt is selected from the group consisting of ammonium, isopropylammonium, ethanolammonium, dimethylammonium, trimethylsulfonium, sodium and potassium, comprising the steps of:

a) forming an anhydrous reaction mixture comprising an acid catalyst, a compound of the following general P—O—P anhydride moieties comprises one P atom at the oxidation state (+III) and one P atom at the oxidation state (+III) or (+V) and is selected from the group consisting of tetraphosphorus hexaoxide, P$_4$O$_7$, P$_4$O$_8$, P$_4$O$_9$, pyrophosphites of general formula (RO)$_2$P—O—P(OR)$_2$ wherein R is an alkyl or aryl group, and combinations thereof, and b) hydrolyzing the compound having the general formula $R^1$—CH$_2$—N(—CH$_2$PO$_3$R$^3_2$)(—CH$_2$—$R^2$) to form N-phosphonomethyliminodiacetic acid or one of its derivatives.

2. The method of claim 1 wherein the $R^1$—CH$_2$—NX—CH$_2$—$R^2$ compound is a 4-X-piperazine-2,6-dione or a 4-X-1-(C$_1$-C$_4$ alkyl)piperazine-2,6-dione.

3. The method of claim 1, wherein ratio of N—X moieties to P—O—P anhydride moieties is between 0.3 and 2.0.

4. The method of claim 1, wherein the compound of the general formula $R^1$—CH$_2$—NX—CH$_2$—$R^2$ is selected from the group consisting of N-hydroxymethyliminodiacetonitrile, N-hydroxymethyliminodiacetic acid, N-hydroxymethyliminodiacetic acid dimethylester, N-hydroxymethyliminodiacetic acid diethylester, N-carboxymethyliminodiacetonitrile, N-carboxymethyliminodiacetic acid dimethylester and N-carboxymethyliminodiacetic acid diethylester.

5. The method of claim 1, wherein the compound comprising the P—O—P anhydride moieties is selected from the group consisting of tetraphosphorus hexaoxide, $P_4O_7$, $P_4O_8$, $P_4O_9$, tetraethylpyrophosphite, and combinations thereof.

6. The method of claim 1, wherein the compound comprising the P—O—P anhydride moieties is tetraphosphorus hexaoxide.

7. The method of claim 1, wherein the acid catalyst is a homogeneous Brønsted acid catalyst selected from the group consisting of methanesulfonic acid, trifluoromethanesulfonic acid, acetic acid, trifluoroacetic acid, p-toluenesulfonic acid, hydrochloric acid, phosphorous acid, phosphoric acid and mixtures thereof.

8. The method of claim 1, wherein the acid catalyst is a heterogeneous Brønsted acid selected from the group consisting of:
   (i) supported or unsupported solid acidic metal oxides;
   (ii) cation exchange resins selected from the group consisting of copolymers of styrene, ethylvinyl benzene and divinyl benzene, functionalized so as to graft $SO_3H$ moieties onto an aromatic group and perfluorinated resins carrying carboxylic and/or sulfonic acid groups;
   (iii) organic sulfonic, carboxylic and phosphonic Brønsted acids, wherein the Brønsted acids are substantially immiscible in the reaction mixture at a reaction temperature;
   (iv) an acid catalyst derived from:
   interaction of a solid support having a lone pair of electrons onto which is deposited an organic Brønsted acid;
   interaction of a solid support having a lone pair of electrons onto which is deposited a compound having a Lewis acid site; or
   heterogeneous solids functionalized by chemical grafting with a Brønsted acid group or a precursor thereof; and
   (v) heterogeneous heteropolyacids of the general formula $H_xPM_yO_z$ wherein P is selected from phosphorus and silicon and M is selected from tungsten and molybdenum and combinations thereof.

9. The method of claim 1, wherein the acid catalyst is a homogeneous Lewis acid selected from the group consisting of $LiN(CF_3SO_2)_2$, $Mg(OCF_3SO_2)_2$, $Al(OCF_3SO_2)_3$, $Bi(OCF_3SO_2)_3$, and $Sc(OCF_3SO_2)_3$.

10. The method of claim 1, wherein the acid catalyst is a heterogeneous Lewis acid obtained from interaction of a homogeneous Lewis acid catalyst and an organic or inorganic polymer compound.

11. The method of claim 1, wherein step a) is carried out in the presence of a solvent selected from the group consisting of 1,4-dioxane, toluene, ethyl acetate, acetonitrile, sulfolane, 1-ethyl-3-methyl-imidazolium bis(trifluoromethylsulfonyl) imide, and mixtures thereof.

12. The method of claim 1, wherein the P—O—P anhydride moiety comprising compound is gradually added to the compound with general formula $R^1$—$CH_2$—NX—$CH_2$—$R^2$ while maintaining a temperature of step a) below 100° C.

13. The method of claim 1, wherein the P—O—P anhydride moiety comprising compound is gradually added in step a) and wherein after completion of addition of the P—O—P anhydride moiety comprising compound, step a) is heated to a temperature between 20° C. and 100° C. and maintained at the temperature for a period of time between 1 hour and 24 hours.

14. The method of claim 1, wherein the hydrolysis of step b) is performed at a temperature between 20° C. and 120° C., for a period between 10 minutes and 24 hours.

15. The method of claim 1, wherein the hydrolysis of step b) is performed under alkali conditions.

16. The method of claim 1, wherein the P—O—P anhydride moiety comprising compound is selected from the group consisting of tetraphosphorus hexaoxide, $P_4O_7$, $P_4O_8$, $P_4O_9$, and combinations thereof.

17. The method of claim 1, further comprising converting the N-phosphonomethyliminodiacetic acid or a derivative thereof to N-(phosphonomethyl)glycine.

18. The method of claim 1, wherein the compound of the following general formula $R^1$—$CH_2$—NX—$CH_2$—$R^2$ is N-hydroxymethyliminodiacetic acid.

19. The method of claim 18, wherein the P—O—P anhydride moiety comprising compound is selected from the group consisting of tetraphosphorus hexaoxide, $P_4O_7$, $P_4O_8$, $P_4O_9$, and combinations thereof.

20. The method of claim 19, wherein the P—O—P anhydride moiety comprising compound is tetraphosphorus hexaoxide.

21. The method of claim 18, further comprising converting the N-phosphonomethyliminodiacetic acid or a derivative thereof to N-(phosphonomethyl)glycine.

* * * * *

UNITED STATES PATENT AND TRADEMARK OFFICE
CERTIFICATE OF CORRECTION

PATENT NO. : 10,364,262 B2  
APPLICATION NO. : 14/415684  
DATED : July 30, 2019  
INVENTOR(S) : Albert Devaux, Sebastian Burck and Patrick Notte Page 1 of 1

It is certified that error appears in the above-identified patent and that said Letters Patent is hereby corrected as shown below:

In the Claims

Column 18, Line 19:
"an alkyl group; and"

Should read:
-- an alkyl group, or an aryl group; and --

Signed and Sealed this  
Tenth Day of March, 2020

Andrei Iancu  
*Director of the United States Patent and Trademark Office*